United States Patent
Bonutti

(10) Patent No.: US 6,217,617 B1
(45) Date of Patent: Apr. 17, 2001

(54) BONE IMPLANT AND METHOD OF SECURING

(76) Inventor: Peter M. Bonutti, 1303 W. Evergreen Plz., Effingham, IL (US) 62401

( * ) Notice: Subject to any disclaimer, the term of this patent is extended or adjusted under 35 U.S.C. 154(b) by 919 days.

(21) Appl. No.: 08/735,916

(22) Filed: Oct. 24, 1996

Related U.S. Application Data

(62) Division of application No. 08/377,759, filed on Jan. 24, 1995, now Pat. No. 5,624,462, which is a division of application No. 08/046,220, filed on Apr. 12, 1993, now Pat. No. 5,441,538.

(51) Int. Cl.$^7$ .................................................. A61F 2/38
(52) U.S. Cl. ............................................................ 623/20.14
(58) Field of Search ............................... 623/16, 18, 20, 623/22, 23; 606/86, 92

(56) References Cited

U.S. PATENT DOCUMENTS

| | | |
|---|---|---|
| 3,698,017 | 10/1972 | Scales et al. . |
| 3,774,244 * | 11/1973 | Walker . |
| 3,869,731 | 3/1975 | Walker . |
| 4,055,862 | 11/1977 | Farling . |
| 4,081,866 | 4/1978 | Upshaw et al. . |
| 4,608,052 * | 8/1986 | Van Kampen et al. ............... 623/16 |
| 4,711,233 * | 12/1987 | Brown . |
| 4,979,957 * | 12/1990 | Hodorek ............................... 623/20 |
| 5,171,276 * | 12/1992 | Caspari et al. . |
| 5,383,937 * | 1/1995 | Mikhail ................................. 623/20 |

* cited by examiner

Primary Examiner—David J. Isabella
(74) Attorney, Agent, or Firm—Tarolli, Sundheim, Covell, Tummino & Szabo L.L.P.

(57) ABSTRACT

The present invention is an implant for securing to a bone to form a plurality of cement cells. The implant has a bone engagement portion for engagement with the bone. The implant has surfaces defining a first plurality of cement compartments in the bone engagement portion for alignment with a second plurality of cement compartments in the bone to form a plurality of cement cells extending between the implant and the bone when the implant is secured to the bone. The cement cells receive cement therein to form plugs of cement extending between the implant and the bone to secure the implant to the bone.

13 Claims, 5 Drawing Sheets

BONE IMPLANT AND METHOD OF SECURING

This is a divisional of application Ser. No. 08/377,759 filed Jan. 24, 1995, now U.S. Pat. No. 5,624,462. The aforementioned application Ser. No. 08/377,759 is itself a divisional of application Ser. No. 08/046,220 filed Apr. 12, 1993, now U.S. Pat. No. 5,441,538. The benefit under Title 35, United States Code, §120 of the above-identified applications is hereby claimed.

BACKGROUND OF THE INVENTION

1. Technical Field

The present invention relates to an implant and to a method of securing an implant to a bone. More particularly, the present invention relates to an implant for securing to bone with bone cement, and to a method of securing an implant to a bone with bone cement.

2. Description of the Prior Art

Implants are often secured to bone with a material such as polymethylmethacrylate (PMMA), hereinafter referred to as "bone cement" or simply "cement". The cement bonds between a surface of the implant and a surface of the bone to secure the implant to the bone.

Often the bone cement is applied as a slab, for example between adjoining flat surfaces of a patellar implant and a patella. There may be defects in the cement such as an air bubble, an impurity or unreacted PMMA powder. It is known for slabs of bone cement to crack. initiates at the site of a defect. Or, a slab of bone cement could fail and crack from other causes such as stress or trauma. If bone cement is present in a continuous mass such as a slab, a crack propagates through the slab, resulting in complete failure of the cement system.

Another concern with bone cement is the maximum force (such as torque) which can be transferred, through the cement, between the implant and the bone. In the case of a slab, the maximum torque is related to the adhesive interfacial shear stress between the cement and the implant.

SUMMARY OF THE INVENTION

It is desirable to be able to minimize propagation through the bone cement of any cracks which may unavoidably occur. To this end, in accordance with the present invention, compartments are formed in the face of the implant adjacent the bone, and in the face of the bone. The two sets of compartments are aligned to form cement cells extending between the implant and the bone when the implant is secured to the bone. The cement cells receive cement therein to form plugs of cement extending between the implant and the bone to secure the implant to the bone.

In one embodiment the present invention is an implant for securing to a bone to form a plurality of cement cells. The implant has a bone engagement portion for engagement with the bone. The implant has surfaces defining a first plurality of cement compartments in the bone engagement portion for alignment with a second plurality of cement compartments in the bone to form a plurality of cement cells extending between the implant and the bone when the implant is secured to the bone. The cement cells receive cement therein to form plugs of cement extending between the implant and the bone to secure the implant to the bone.

The implant may include one or more fill ports for supplying cement to one or more of the cement compartments. The implant may include means for allowing excess cement to flow from the cement compartments away from the bone engagement portion, such as exit channels extending from the cement compartments in a direction away from the bone engagement portion. The implant may include ridge portions around the cement compartments in the implant to block flow of cement out of the cement compartments and between the implant and the bone. There may be respective alignment markers on the bone and on the implant for aligning the cement compartments in the implant with the cement compartments in the bone.

The bone engagement portion of the implant is preferably in abutting engagement with the bone so that there is not a continuous layer of cement between the implant and the bone across the full extent of the interface between the implant and the bone. This discontinuity in the layer of bone cement inhibits crack propagation.

In another embodiment, the present invention is a combination including an implant having a bone engagement portion for engagement with a bone and a first plurality of cement compartments in the bone engagement portion; a bone having a second plurality of cement compartments; the cement compartments in the implant being aligned with the cement compartments in the bone to form cement cells extending between the implant and the bone; and plugs of cement in the cement cells extending between the implant and the bone and securing the implant to the bone.

In another embodiment, the present invention is a method of securing an implant to bone comprising the following steps: providing an implant having a bone engagement portion for engagement with the bone and having surfaces defining a first plurality of cement compartments in the bone engagement portion; making a second plurality of cement compartments in the bone; placing the bone engagement portion of the implant adjacent the bone; aligning the cement compartments in the implant with the cement compartments in the bone to form cement cells extending between the implant and the bone; and placing cement in the cement cells to form plugs of cement extending between the implant and the bone to secure the implant to the bone. Preferably, the method includes blocking cement from entering between the implant and the bone sufficiently to ensure that there is not a continuous layer of cement between the implant and the bone over the full extent of the interface between the implant and the bone.

The cement compartments in the bone may be formed by drilling, broaching, or pressing into the bone. The cement compartments are preferably cylindrical because that shape can easily be made with a standard drill. However, other shapes are possible.

With a compartmentalized system, the strength of the implant/bone interface is governed by not only the adhesive shear stress but also the pure shear stress of the plugs of bone cement. The interface strength is enhanced by the pure shear strength of the plugs of bone cement. For an aligned compartment system to fail in shear the cement plugs must fail in shear which requires substantially more stress than that needed to cause failure of a slab.

BRIEF DESCRIPTION OF THE DRAWINGS

The foregoing and other features of the present invention will become apparent to one skilled in the art to which the present invention relates upon consideration of the following description of the invention with reference to the accompanying drawings, wherein:

FIG. 2 is a sectional view of the implant of FIG. 1 being applied to a bone having three matching cement compartments, and bone cement between;

DESCRIPTION OF PREFERRED EMBODIMENT

Figure 1:
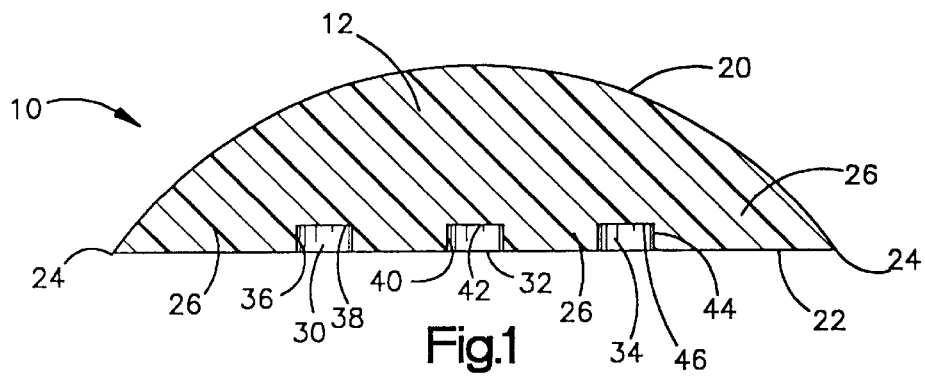
FIG. 1 is a sectional view of an implant having three cement compartments.

The present invention relates to an implant and to a method of securing an implant to a bone with bone cement. The present invention is applicable to various implant constructions. As representative of the present invention, FIG. 1 illustrates a patellar implant 10. The implant 10 is made of a body of material 12. The material 12 is preferably a biocompatible plastic material. A preferred material is ultra high molecular weight polyethylene (UHMWPE). Alternatively, the implant 10 can be a metal backed plastic component having a bone engagement portion made of metal and an articulating surface made of plastic.

The implant 10 has an arcuate articulating surface 20 and a planar bone engagement surface 22. The surfaces 20 and 22 intersect at the outer periphery 24 of the implant 10.

A bone engagement portion 26 of the implant 10 includes the portion of the implant 10 adjacent to or close to the bone engagement surface 22. The bone engagement portion 26 includes surfaces defining a plurality of cement compartments or recesses 30, 32, and 34 in the implant 10.

Each of the cement compartments or recesses 30, 32, and 34 is generally cylindrical in shape, and extends inwardly into the body of material 12 from the bone engagement surface 22. The cement compartment 30 is defined by a cylindrical side wall 36 which extends between a planar end wall 38 and the plane of the bone engagement surface 22. The bone engagement surface 22 is removed during formation of the cement compartment 30 at the location of the cement compartment 30, within the boundaries of the cylindrical side wall 36, so that cement (not shown in FIG. 1) can be placed into the cement compartment 30 in a direction from the bone engagement surface 22 toward the interior of the body of material 12 of the implant 10.

The cement compartments or recesses 32 and 34 are similar to the cement compartment or recess 30. The cement compartment 32 is defined by a cylindrical side wall 40 extending between a planar end wall 42 and a circular rim at the plane of the bone engagement surface 22. The cement compartment 34 is defined by a cylindrical side wall 44 extending between a planar end wall 46 and a circular rim at the plane of the bone engagement surface 22.

Figure 2:
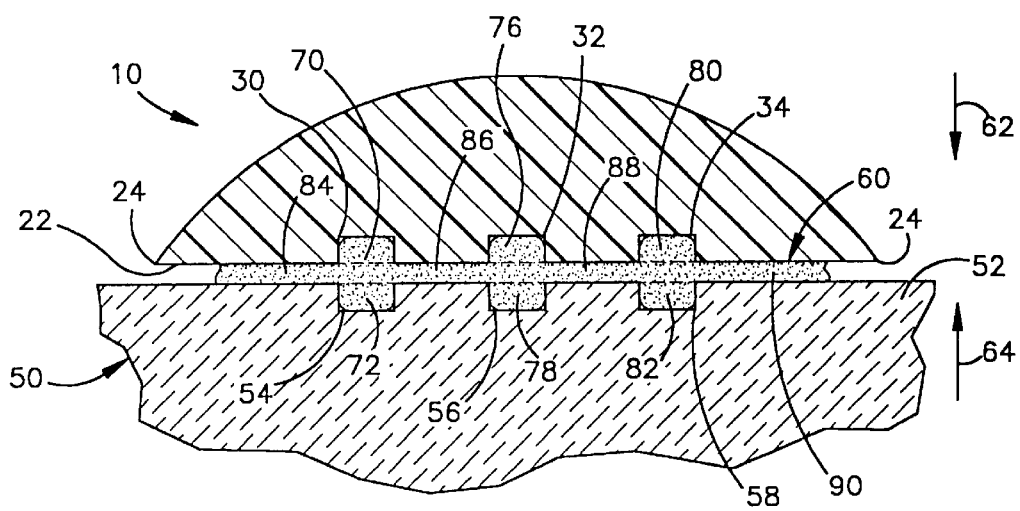

The patellar implant 10 is designed to be implanted on a resected patella (kneecap) 50 shown fragmentarily in FIG. 2. The patella 50 is resected to provide a planar implant engagement surface 52 for mating with the bone engagement surface 22 of the implant 10.

Figure 5:
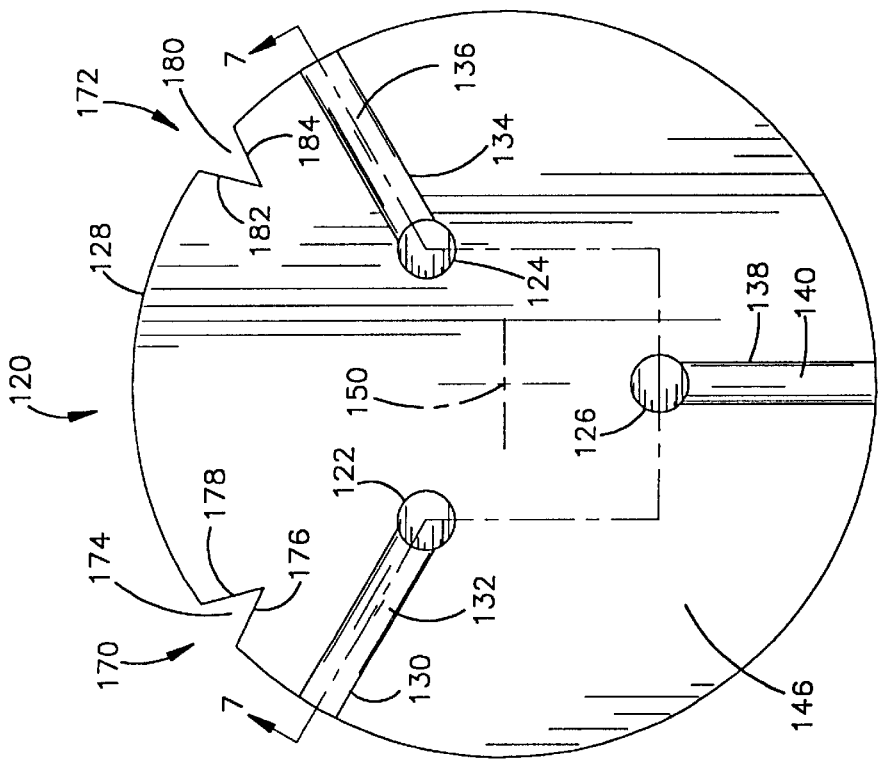
FIG. 5 is an end view of an implant like the implant of FIG. 1 but having individual fill ports for three cement compartments.

In preparation for implanting the implant 10 on the patella 50, a plurality of cement compartments or recesses 54, 56, and 58 are formed in the patella 50. The cement compartments or recesses 54, 56, and 58 are similar in size and shape to the cement compartments 30, 32, and 34 in the implant 10. Further, the cement compartments 54, 56, and 58 in the patella 50 are located in the patella 50 so as to be aligned with the respective cement compartments 30, 32, and 34 in the implant 10 when the implant 10 is placed adjacent the patella 50. For example, there may be provided three cement compartments in an implant as shown in FIG. 5, for alignment with three cement compartments in a bone shown in FIG. 6.

To secure the implant 10 (FIG. 2) to the patella 50, a quantity of bone cement 60 is placed between the implant and the patella. The implant 10 and the patella 50 are then moved toward each other in the direction indicated by the arrows 62 and 64 (FIG. 2).

The quantity of bone cement 60 may be placed on the implant engagement surface 52 of the patella 50, with the implant 10 being then moved in the direction indicated by the arrow 62 into engagement with the bone cement. Alternatively, the bone cement 60 may be placed on the bone engagement surface 22 of the implant 10, and the implant and bone cement then moved in the direction indicated by the arrow 62 into engagement with the bone 50. There may, of course, be movement of the patella 50 in the direction indicated by the arrow 64 to join the patella with the implant 10; such movement may be limited by the soft tissue attachment of the patella to the patient's knee joint. Some cement 60 may be placed on the implant 10 and the remainder of the cement placed on the patella 50, with the implant and patella then being pressed or squeezed toward each other.

When the implant 10 and the bone 50 are in the position shown in FIG. 2, the bone engagement surface 22 of the implant is spaced from the implant engagement surface 52 of the bone, with the bone cement 60 disposed therebetween. A portion 70 of the bone cement 60 is disposed in the cement compartment 30 in the implant 10. A portion 72 of the bone cement 60 is disposed in the cement compartment 54 in the bone 50, which is aligned with the cement compartment 30. A portion 76 of the bone cement 60 is disposed in the cement compartment 32 of the implant 10. A portion 78 of the bone cement 60 is disposed in the cement compartment 56 of the bone 50, which is aligned with the cement compartment 32. A portion 80 of the bone cement 60 is disposed in the cement compartment 34 in the implant 10. A portion 82 of the bone cement 60 is disposed in the cement compartment 58, which is aligned with the cement compartment 34.

When the implant 10 and the bone 50 are in the relative position shown in FIG. 2, there is some bone cement disposed between the bone engagement surface 22 of the implant and the implant engagement surface 52 of the bone. A portion 84 of the bone cement 60 is disposed between the bone engagement surface 22 and the bone 50 and extends outwardly from the aligned cement compartments 30 and 54. Another portion 86 of the bone cement 60 extends between the aligned compartments 30 and 54 and the aligned cement compartments 32 and 56. A further portion 88 of the bone cement 60 is disposed between the aligned cement compartments 32 and 56 and the aligned cement compartments 34 and 58. Another portion 90 of the bone cement 60 extends outwardly from the aligned cement compartments 80 and 82 toward the outer edge 24 of the implant 10.

Figure 3:
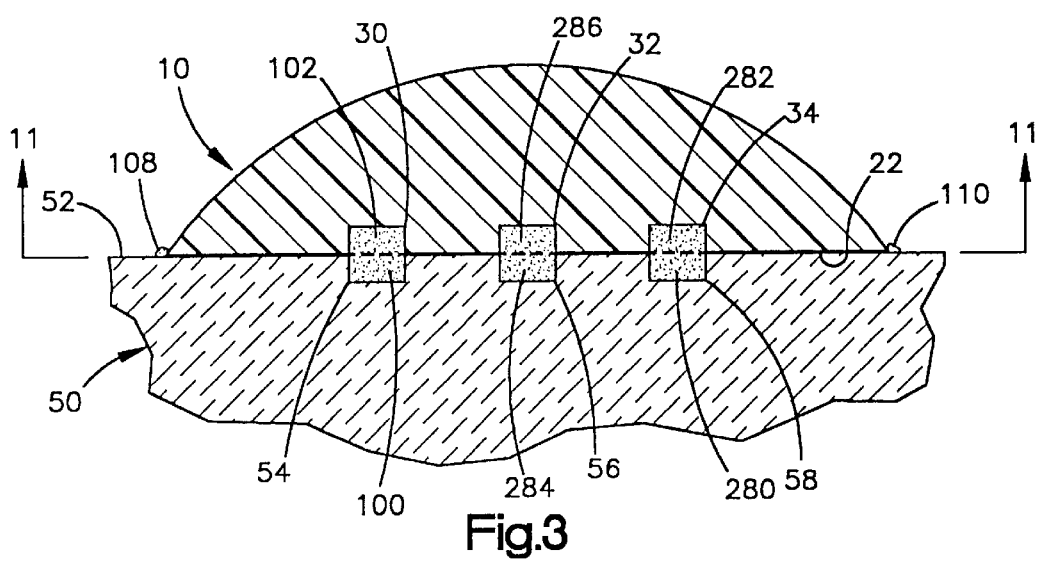
FIG. 3 is a view similar to FIG. 2 after the implant is moved to a position against the bone to form cement cells filled with bone cement.

The implant 10 is pressed or squeezed firmly against the bone 50 as shown in FIG. 3 to remove as much bone cement as possible from between the bone engagement surface 22 of the implant and the implant engagement surface 52 of the bone. The amount of excess bone cement 60, that is the bone cement which is not disposed within the various cement compartments when the implant 10 and the bone 50 are adjacent each other as in FIG. 3, depends on the amount of cement initially placed between the implant and the bone, and its location. Ideally, all the cement flows into the aligned cement compartments, but of course this may not be possible.

Figure 4:
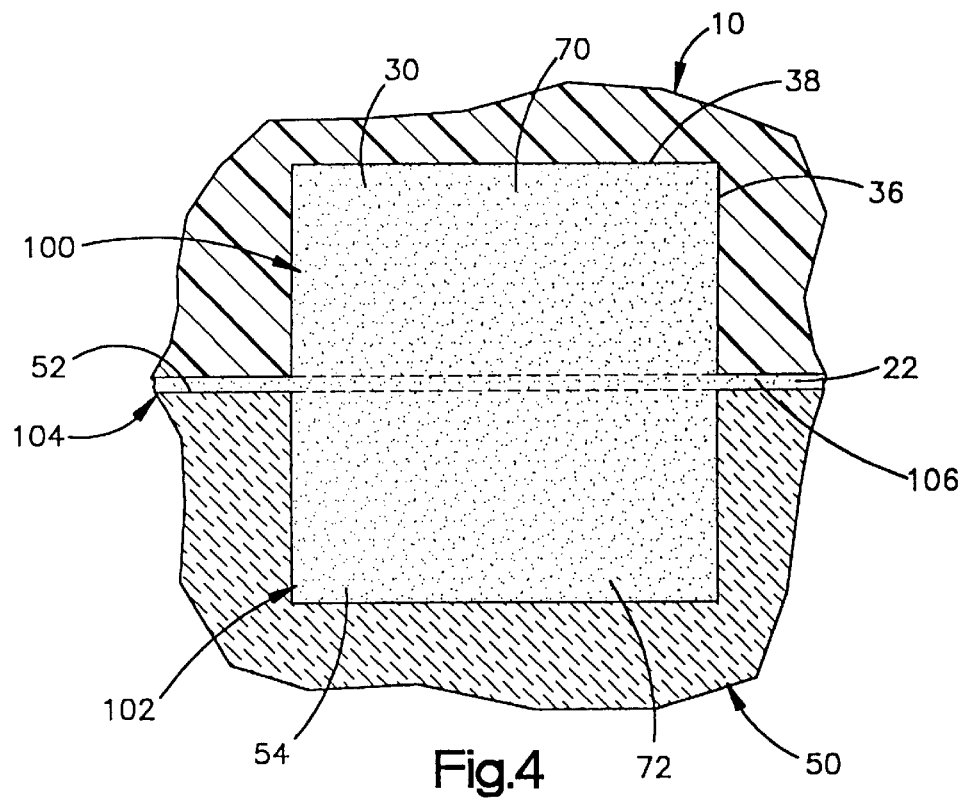
FIG. 4 is an enlarged view of one filled cement cell.

When the implant 10 is adjacent the bone 50, the cement compartment 30 in the implant is aligned with the cement compartment 54 in the bone to form a cement cell 100. The cement cell 100 extends between the implant 10 and the bone 50. Disposed within the cement cell 100 (FIG. 4) is a plug or pin of cement 102 which includes the cement portion 70 in the cement compartment 30 of the implant 10 and the cement portion 70 in the cement compartment 54 of the bone 50. The cement cell 100 extends between the implant 10 and the bone 50 across the interface 104 between the implant and the bone—that is, across the area of engagement between the implant and the bone.

Figure 11:
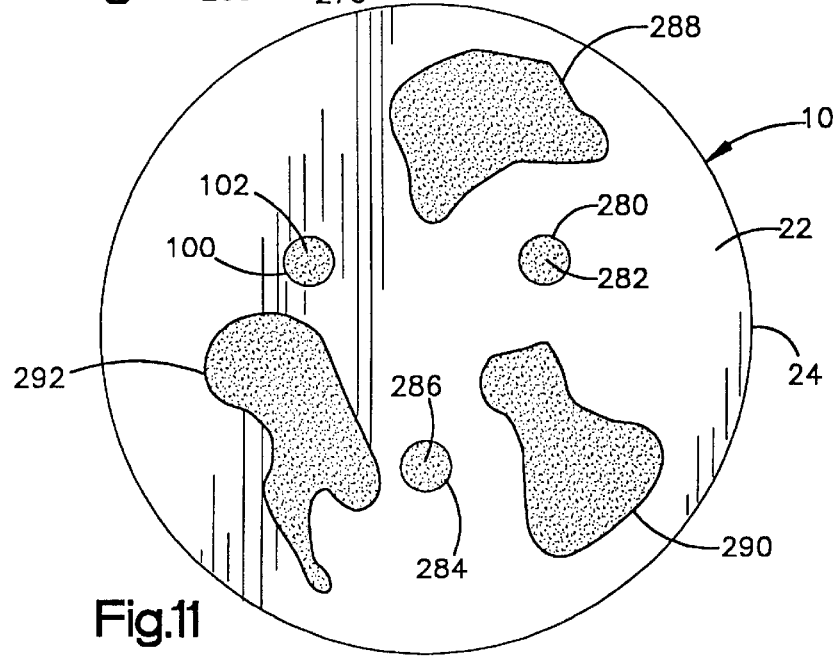
FIG. 11 is a sectional view taken along line 11—11 of FIG. 3 and showing areas of discontinuity in the layer of bone cement.

A very thin layer 106 of bone cement 60 may be disposed between the bone engagement surface 22 of the implant 10 and the implant engagement surface 52 of the bone 50. This can be for several reasons. First, it may not be possible to provide matching planar surfaces on the implant 10 and on the bone 50 so as to allow complete contact of the two elements at all locations. Second, the implant 10 and bone 50 may be pressed toward each other unevenly, with more pressure at some locations and less at other locations. In any event, it is desirable that there not be a continuous layer of bone cement 60 between the implant 10 and the bone 50 for the entire extent of the interface between the implant and the bone. Thus, as seen in FIG. 11, areas of discontinuity of the bone cement are preferably present, to block propagation of any cracks throughout the entire interface. Any bone cement which squeezes out to the other edge 24 of the implant, as indicated at 108 and 110 in FIG. 3, is cleaned off.

With the prior art method of using a slab of cement between the implant and the bone, it was necessary to hold the implant away from the bone by at least some distance. With the present invention, the cement plugs make it possible to put the implant directly against the bone. This allows for minimizing the areas of continuity of bone cement between the implant and the bone. This minimizes the likelihood of propagation of a crack in the bone cement and minimizes the chance of failure of the cement system.

The plugs or pins of cement, such as the cement plug 102 in the cement cell 100, provide additional stability to secure the implant 10 to the bone 50. In the case of a slab of cement only between an implant and a bone, the maximum force, such as torque, which can be transferred through the cement between the implant and the bone, is related to the adhesive interfacial shear stress between the cement and the implant. With a compartmentalized system, as illustrated in the drawings, the strength of the implant/bone interface is governed by not only the adhesive shear stress but also the pure shear stress of the plugs or pins or cylinders of bone cement in the cement cells. For a system using aligned compartments, as illustrated, to fail in shear, the cement pins must fail in shear. This requires substantially more stress than that needed to cause failure of the slab.

Figure 7:
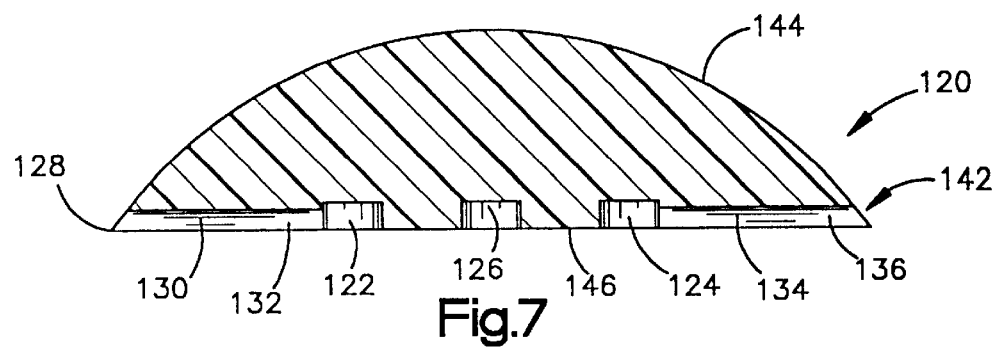
FIG. 7 is a view taken along line 7—7 of FIG. 5.

Bone cement may be placed in the cement cells in a manner other than as described above. The implant 120 (FIGS. 5, 7 and 8) has three cement compartments or recesses 122, 124, and 126 which are similar in size, shape and location to the cement compartments or recesses 30, 32 and 34 of the implant 10 (FIGS. 1–4). However, the cement compartments in the implant 120 are fillable through fill ports extending between the respective cement compartments and the radially outer edge 128 of the implant 120.

A first fill port 130 (FIG. 5) is defined by a partial cylindrical surface 132 extending radially outwardly from the cement compartment 122 to the implant periphery 128. A second fill port 134 extends radially between the cement compartment 124 and the periphery 128 and is partially defined by a partial cylindrical surface 136. A third fill port 138, partially defined by a partial cylindrical surface 140, extends radially between the cement compartment 126 and the implant periphery 128.

The cement compartments or recesses 122, 124, and 126, with their respective fill ports 130, 134, and 138, are disposed in a bone engagement portion 142 of the implant 120. The bone engagement portion 142 is the lower portion (as viewed in FIG. 7) of the implant 120. The implant 120 also has an arcuate articulating surface 144 and a generally planar bone engagement surface 146.

As can be seen in FIG. 5, the implant 120 has a circular shape in plan. The cement compartments or recesses 122, 124, and 126 are spaced equally about a central axis 150 of the implant 120. The cement compartments 122, 124, and 126 are designed to mate with matching cement compartments or recesses 154, 156, and 158 in a bone 160 (FIG. 6) having an implant engagement surface 162.

To aid in alignment of the cement compartments or recesses in the implant 120 with the cement compartments or recesses in the bone 160, one or more alignment markers may be provided on either the implant or the bone or both. The implant 120 (FIG. 5) has two alignment markers 170 and 172. The alignment marker 170 is a notch 174 cut into the periphery 128 of the implant 120 and defined by two side lines 176 and 178. The alignment marker 172 is a notch 180 cut into the periphery 128 of the implant 120 and defined by two side lines 182 and 184.

A template (not shown) is used to place alignment markers 186 and 188 (FIG. 6) on the bone 160, preferably at the same time as the cement compartments or recesses 154, 156, and 158 are made. The alignment marker 186 is a notch 190 defined by two side lines 192 and 194 scribed into the implant engagement surface 162 of the bone 160. The alignment marker 188 is a V-shaped notch 196 defined by two side lines 198 and 200 scribed into the implant engagement surface 162 of the bone 60.

Figure 6:
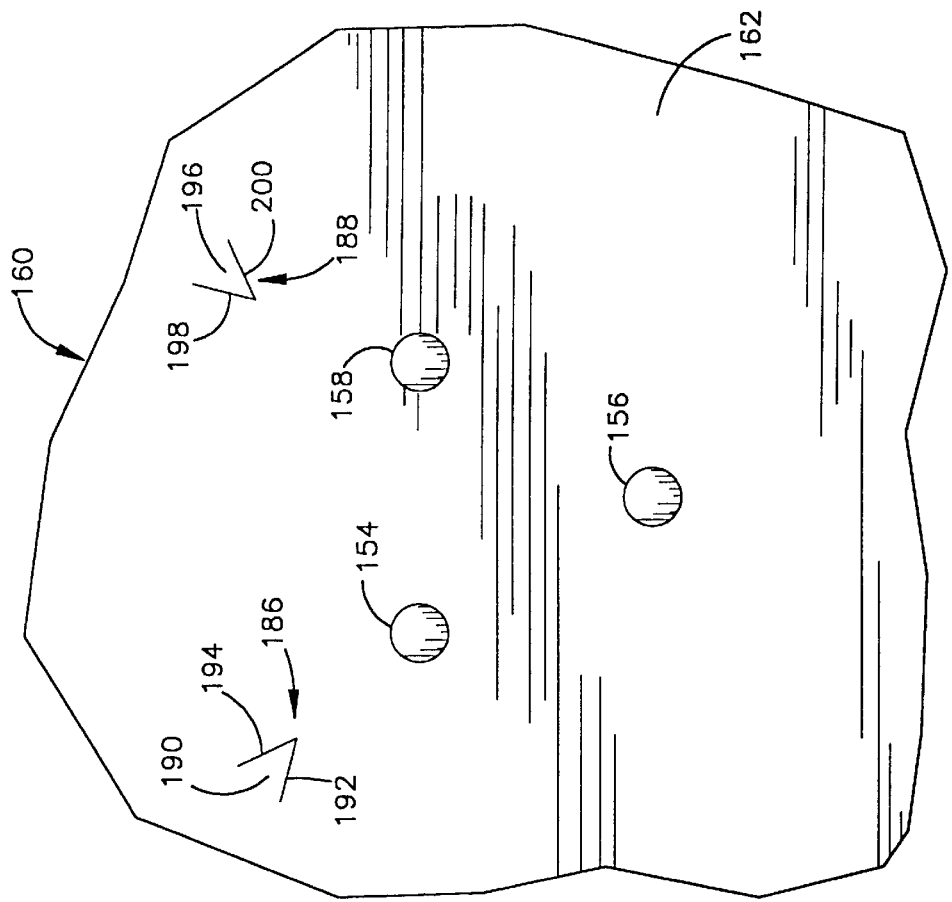
FIG. 6 is an end view of a bone portion having three cement compartments.

The implant 120 in FIG. 5 is aligned with or placed on the bone 160 in FIG. 6 by rotating or mirroring the implant 120 about an imaginary line extending vertically on the sheet of drawings between FIGS. 5 and 6. The alignment marker 172 is placed on and in alignment with the alignment marker 186. The alignment marker 170 of the implant 120 is placed on and in alignment with the alignment marker 188 on the bone 160.

When this is done, the cement compartment 124 of the implant 120 is aligned with the cement compartment 154 on the bone 160. Similarly, the cement compartments or recesses 122 and 126 of the implant 120 are aligned with, respectively, cement compartments or recesses 158 and 156 of the bone 160. The cement compartment 122 in the implant 120 aligns with the cement compartment 154 in bone 160 to form a cement cell 164. The cement compartment 126 in the implant 120 aligns with the cement compartment 156 in the bone 160 to form a second cement cell 166. The cement compartment 124 in the implant 120 aligns with the cement compartment 158 in the bone 160 to form a third cement cell 168.

After the implant 120 is aligned with the bone 160 (FIG. 8), the cement cells or recesses 164, 166, and 168 are filled with bone cement in a manner as described below to secure the implant to the bone. The cement cell 164 is filled through the fill port 130. The cement cell 166 is filled through the fill port 138 (FIG. 5) for the cement compartment 126. The cement cell 168 is filled through the fill port 134.

Figure 8:
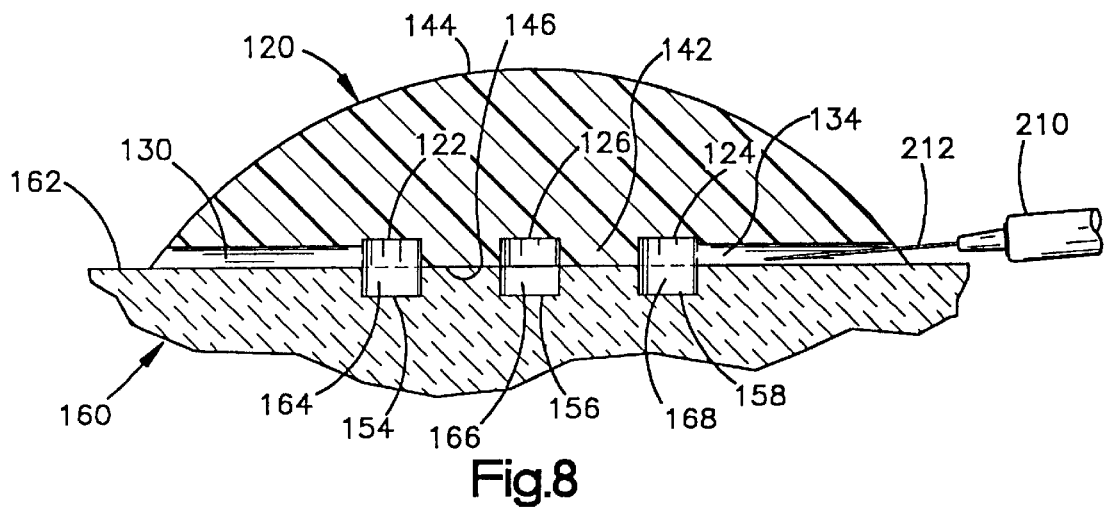
FIG. 8 illustrates filling of one of the cement compartments of the implant of FIGS. 5 and 7.

As illustrated schematically in FIG. 8, a device is used to introduce cement into the cement cells of the aligned implant 120 and bone 160. The device may be a syringe 210 having a needle 212 which is inserted into the fill port 134, for example. Bone cement (not shown) is injected through the syringe 210 and the needle 212 to fill the cement cell 168. Excess bone cement will be present in the fill port 134. Similarly, the cement cell 164 is filled through the fill port 130, and the cement cell 166 is filled through the fill port 138 (FIG. 5).

When the cement cells or recesses 164, 166, and 168 are filled, there are plugs or pins or cylinders of bone cement in each of the cement cells. These cement plugs are separated from each other by the solid material of the bone engagement portion 142 of the implant 10. Thus, there is not a continuous layer of bone cement across the interface between the implant 120 and the bone 160. Rather, there are discrete, separated bone cement portions securing the implant 120 to the bone 160. These bone cement portions include plugs of cement in the cement cells 164, 166, and 168. These plugs of cement extend between the implant 120 and the bone 160, away from the bone engagement surface 146 and the implant engagement surface 162. These cement plugs block lateral movement of the implant 120 relative to the bone 160 in a manner superior to the blocking effect obtained by a simple slab of bone cement between the implant and the bone, as is done in the prior art.

Figure 9:
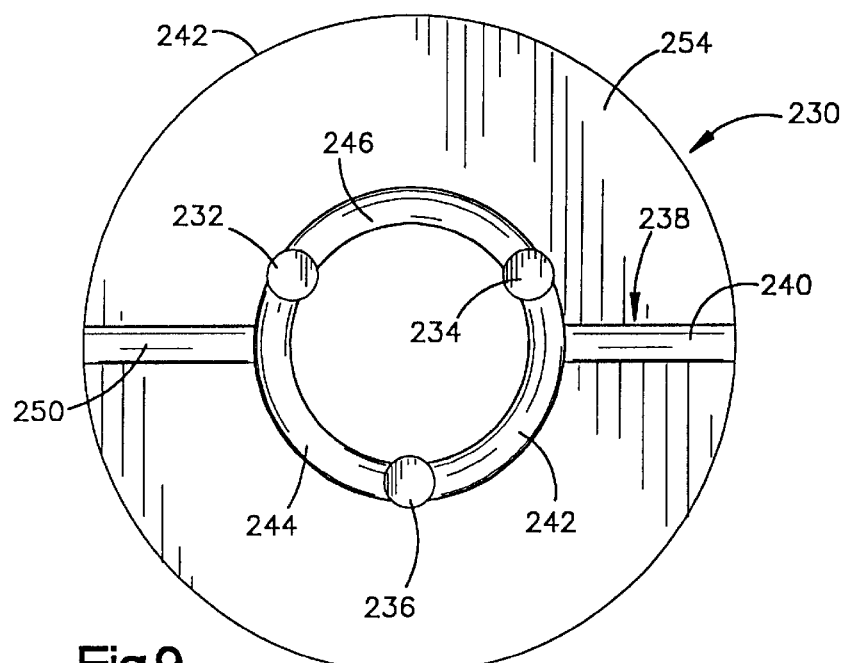
FIG. 9 is a view of an implant having one fill port and one exit channel for three cement compartments.
Figure 10:
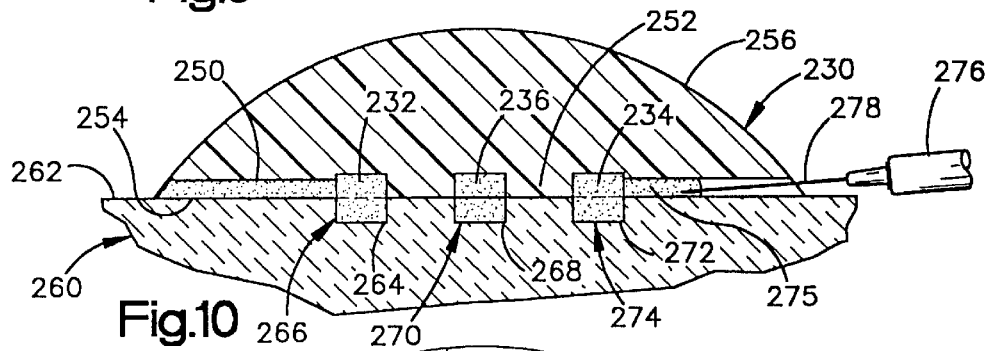
FIG. 10 illustrates the filling of the cement compartments of the implant of FIG. 9.

FIGS. 9 and 10 illustrate another embodiment of the invention in which an implant 230 has three cement compartments or recesses 232, 234, and 236 which are all filled via one fill port 238. The fill port 238 includes a straight portion 240 extending from the outer periphery 242 of the implant 230 to a first arcuate fill port portion 242. The first arcuate fill port portion 242 extends between and interconnects the cement compartments 234 and 236. A second arcuate fill port portion 244 extends between and interconnects the cement compartment 236 and the cement compartment 232. A third arcuate fill port portion 246 extends between and interconnects the cement compartment 234 and the cement compartment 232. An exit channel 250 extends from the portion 244 of the fill port 238 to the outer periphery 242 of the implant 230, at a location diametrically opposite from the fill port portion 240. The implant 230 has a bone engagement portion 252, a bone engagement surface 254, and an articulating surface 256.

FIG. 10 illustrates the securing of the implant 230 to a bone 260. The bone 260 has an implant engagement surface 262 which is placed in mating engagement with the bone engagement surface 254 of the implant 230. The implant 230 is aligned with the bone 260 so that the cement compartment or recess 232 aligns with a cement compartment or recess 264 in the bone 260 to form a cement cell 266 extending between the implant 230 and the bone 260. The cement compartment or recess 236 in the implant 230 aligns with a cement compartment 268 in the bone 260 to form a cement cell 270 extending between the implant and the bone. The cement compartment or recess 234 in the implant 230 aligns with a cement compartment or recess 272 in the bone 260 to form a cement cell 274 extending between the implant and the bone.

The cement cells or recesses 266, 270 and 274 are filled by insertion of bone cement 275 through a device such as a syringe 276 (FIG. 10) having a needle 278. The needle 278 is placed in the fill port portion 240 and bone cement 275 is injected into the fill port portion 240. As bone cement 275 continuous to be injected, it flows through the remaining portions 242, 244 and 246 of the fill port 238. The cement cells or recesses 266, 270 and 274 fill with bone cement 275. Excess cement 275 flows outwardly from the fill port 238 through the exit channel 250 and may be cleaned off the outer surface 256 of the implant 230.

FIG. 11 illustrates how the present invention can minimize the possibility of there being a continuous layer of bone cement across the entire extent of the interface between an implant and a bone. The cement cell 100 (FIGS. 3 and 11) is filled with a plug or pin of bone cement 102. Similarly, the cement compartments 34 and 58 (FIG. 3) form a cement cell 280 (FIGS. 3 and 11) filled with a plug of cement 282. The cement compartments 32 and 56 (FIG. 3) form a cement cell 284 (FIGS. 3 and 11) filled with a plug of bone cement 286. The plugs of bone cement 102, 282, and 286 are discrete and separate from each other. There is no continuous body of bone cement extending between any two of the plugs of bone cement 102, 282, and 286. There may be other areas of bone cement disposed between the bone engagement surface 22 of the implant 10 and the implant engagement surface 52 of the bone 50, such as the areas of bone cement indicated schematically at 288, 290 and 292 in FIG. 11. However, these areas of bone cement again do not form one continuous body of bone cement across the extent of the interface between the implant 10 and the bone 50. Thus, any crack which might originate in any one of the bodies of bone cement are not likely to propagate across the entire extent of the interface between the implant 10 and the bone 50.

An implant in accordance with the present invention may include ridge portions around cement compartments in the implant to block flow of cement out of the cement compartment between the implant and the bone. One such ridge portion is illustrated schematically in FIGS. 12 and 13. An implant 300 is disposed in mating engagement with a bone portion 302. The implant 300 has a bone engagement surface 304 disposed adjacent an implant engagement surface 306 of the bone portion 302. A cement compartment 308 in the implant 300 is aligned with a cement compartment 310 in the bone portion 302.

The aligned cement compartments 308 and 310 together define a cement cell 312 having a quantity of bone cement 314 therein. The plug of bone cement 314 extends between the implant 300 and the bone portion 302. The plug of bone cement 314 extends into the implant 300 for a substantial distance in a direction away from the interface or area of engagement 316 between the implant 300 and the bone portion 302. The plug of cement 314 also extends into the bone portion 302 in a direction away from the interface 316, the bone engagement surface 304 and the implant engagement surface 306.

Figure 12:
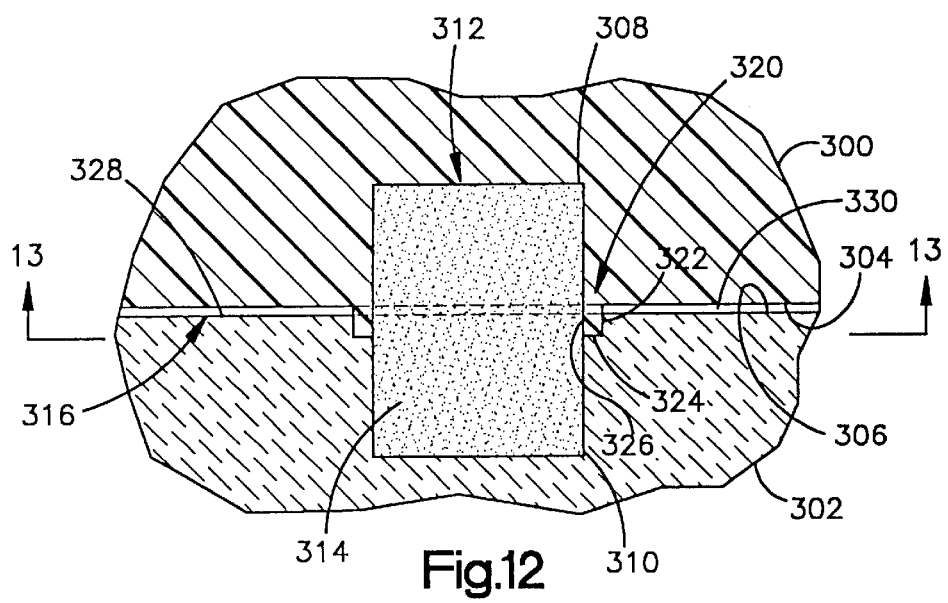
FIG. 12 is a sectional view similar to FIG. 4 and showing an implant having a projecting ridge around its cement compartment to block lateral cement flow.
Figure 13:
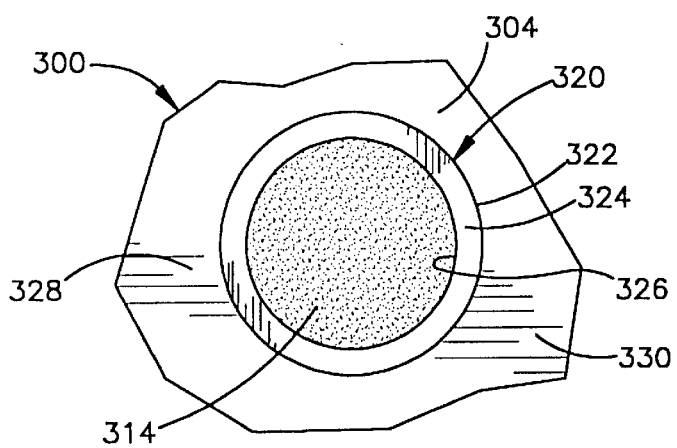
FIG. 13 is a view taken along line 13—13 of FIG. 12.

The implant 300 has a ridge portion 320 extending around the cement compartment 308. The ridge portion 320 has an outer cylindrical surface 322 extending outwardly from the implant bone engagement surface 304; an annular end face 324 extending radially inwardly from the surface 322; and an inner cylindrical surface 326 extending parallel to the outer cylindrical surface 322 from the annular end face 324 to the plane of the bone engagement surface 304. The implant ridge portion 320 extends into the bone portion 302, below the implant engagement surface 306, as illustrated in FIG. 12, when the implant 300 is positioned adjacent the bone portion 302. The ridge portion 320 blocks the flow of cement out of the cement cell 312 into the areas 328 and 330 adjacent the cement cell and between the implant 300 and the bone 302. The ridge portion 320 is pressed into the bone portion 302, below the implant engagement surface 306, when the implant 300 is positioned adjacent the bone 302. Ridge portions may also be provided on fill ports.

Figure 14:
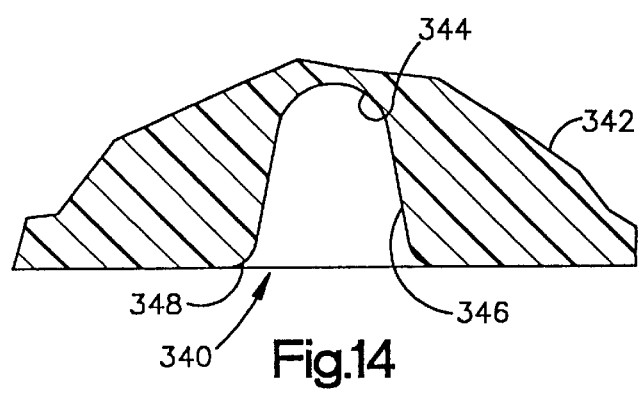
FIG. 14 is a view showing a rounded-bottom cement compartment in an implant.

The cement cells and the cement compartments need not have a cylindrical configuration as illustrated above. FIG. 14 illustrates a cement compartment 340 in an implant 342. The cement compartment or recess 340 has a rounded bottom portion 344 to reduce stress concentrations in the plug of bone cement and/or in the implant itself. Also, the cement compartment 340 has a tapered side wall 346 and an arcuate entrance edge 348. The round cross-sectional shape of the illustrated cement compartments is a result of the drilling process used to form them. Other shapes could be used as suitable and feasible.

As discussed, one embodiment of the invention is in a patellar implant. Typical outer diameters of patellar implants would be 32 mm, 35 mm, and 38 mm to fit different size patients. The height of the implant would be between 6 mm and 8 mm.

Compartment diameters currently being considered are under 10 mm, with a preferred range being between 6 mm and 8 mm. The compartments have a height of 1, 2, or 3 mm in each of the implant and the bone. Thus, the cement cells have a height of 2 mm, 4 mm, or 6 mm. The fill ports are preferably 3 mm to 5 mm in diameter with a height of 2 mm to 3 mm.

The angular placement of the compartments and of the fill ports depend on the number of each. The fill ports could be spaced equally along an imaginary circle as illustrated in the drawings. Alternatively, there could be a large number of smaller compartments spread over the surface, as on the surface of a golf ball.

The presently preferred implant design includes 3 cement compartments with a height of 2 mm and a diameter of 7–8 mm, providing cement cells with a height of 4 mm. Fill ports are not used. The implant is solid UHMWPE with a maximum thickness of 6–8 mm and an outer diameter of 32, 35, or 38 mm depending on the bone size. Alignment is made by two small notches 90° apart on the implant and on the bone.

From the above description of the invention, those skilled in the art will perceive improvements, changes and modifications in the invention. Such improvements, changes and modifications within the skill of the art are intended to be covered by the appended claims.

I claim:

1. An apparatus for connection with a bone having an array of recesses, said apparatus comprising an implant having a side and an array of recesses which extend from said side into said implant, said array of recesses in said implant having a configuration which corresponds to a configuration of the array of recesses in the bone to enable said implant to be positioned relative to said bone with the array of recesses in said implant aligned with the array of recesses in the bone, each of said recesses in said implant having an open end portion and a closed end portion disposed in said implant at a location spaced from said side of said implant, said open end portion of each of said recesses being spaced from open end portions of adjacent recesses, said open end portion of each of said recesses having rim portion which extends completely around the open end portion of each of said recesses, and a plurality of bodies of cement to retain said implant against movement relative to the bone, each of said bodies of cement having an inner end portion which is disposed in one of said recesses in said implant and an outer end portion having surface means for engaging one of the recesses in the bone.

2. An apparatus as set forth in claim 1 wherein said bodies of cement are spaced apart from each other and are free of cement extending between said bodies of cement.

3. An apparatus as set forth in claim 2 wherein each of said recesses in said implant and each of the recesses in the bone have the same configuration.

4. An apparatus as set forth in claim 1 wherein each of said recesses in said implant has a generally cylindrical configuration and each of the recesses in the bone has a generally cylindrical configuration, each of said bodies of cement having a circular side surface area which engages one of said recesses in said implant and a circular side surface area which engages one of the recesses in the bone.

5. An apparatus as set forth in claim 1 wherein said implant has an arcuate articulation surface disposed on a side of said implant opposite from said side from which said array of recesses in said implant extends into said implant.

6. An apparatus as set forth in claim 1 wherein said implant has a peripheral edge portion which intersects said side of said implant and at least partially encloses said array of recesses in said implant, said implant having an arcuate articulation surface which extends to said peripheral edge portion of said implant and extends across said recesses in said array of recesses in said implant.

7. An apparatus for connection with a bone having a plurality of recesses and disposed in a patient's body, said apparatus comprising an implant having a plurality of spaced apart recesses extending into said implant from a side surface of said implant, and connector means for interconnecting said implant and the bone in the patient's body, said connector means includes a plurality of spaced apart bodies of cement, each of said bodies of cement having a first end portion with surface means for engaging one of the recesses in the bone in the patient's body and a second end portion disposed in one of said recesses of said plurality of recesses in said implant.

8. An apparatus as set forth in claim 7 further including a plurality of channels formed in said implant, said channels extend between said recesses in said implant and a peripheral edge portion of said implant to enable cement to be conducted along said channels to said recesses in said implant when said implant is positioned in engagement with the bone in the patient's body.

9. An apparatus comprising an implant having a flat side surface and a plurality of spaced apart cylindrical recesses which extend into said implant from said flat side surface, and connector means for interconnecting said implant and a bone in a patient's body, said connector means including a plurality of separate spaced apart bodies of cement which are free of cement extending between said bodies of cement, each of said bodies of cement having a first cylindrical end portion for engagement with a cylindrical recess in the bone in the patient's body and a second cylindrical end portion disposed in a cylindrical recess in said implant.

10. An apparatus comprising an implant having surface means for engaging areas on a bone in a patient's body and a plurality of recesses which extend inward from said surface means into said implant, and connector means for interconnecting said implant and the bone in the patient's body while said surface means is disposed in engagement with the areas on the bone in the patient's body, said connector means including a plurality of separate bodies of cement which are free of cement interconnecting the bodies of cement, each of said bodies of cement having a first end portion for engagement with a recess in the bone in the patient's body and a second end portion disposed in one of said recesses in said implant.

11. An apparatus for connection with a bone having an array of recesses, said apparatus comprising an implant having a side and an array of recesses which extend from said side into said implant, said array of recesses in said implant having a configuration which corresponds to a configuration of the array of recesses in the bone to enable said implant to be positioned relative to said bone with the array of recesses in said implant aligned with the array of recesses in the bone, each of said recesses in said implant having an open end portion and a closed end portion disposed in said implant at a location spaced from said side of said implant, said open end portion of each of said recesses being spaced from open end portions of adjacent recesses, and a plurality of bodies of cement to retain said implant against movement relative to the bone, each of said bodies of cement having an inner end portion which is disposed in one of said recesses in said implant and an outer end portion having surface means for engaging one of the recesses in the bone, said implant includes a plurality of ridges each of which extends around an open end portion of one of said recesses in said implant, each of said ridges also extends around an open end portion of one of the recesses in the bone.

12. An apparatus for connection with a bone having an array of recesses, said apparatus comprising an implant having a side and an array of recesses which extend from said side into said implant, said array of recesses in said implant having a configuration which corresponds to a configuration of the array of recesses in the bone to enable said implant to be positioned relative to the bone with the array of recesses in said implant aligned with the array of recesses in the bone, each of said recesses in said implant having an open end portion and a closed end portion disposed in said implant at a location spaced from said side of said implant, said open end portion of each of said recesses being spaced from open end portions of adjacent recesses, said open end portion of each of said recesses having a rim portion which extends completely around the open end portion of each of said recesses, a plurality of bodies of cement to retain said implant against movement relative to the bone, each of said bodies of cement having an inner end portion which is disposed in one of said recesses in said implant and an outer end portion having surface means for engaging one of the recesses in the bone, a plurality of channels formed in said implant, said channels extend between said recesses in said implant and a peripheral edge portion of said implant to enable cement to be conducted between said peripheral edge portion of said implant and said recesses.

13. An apparatus for connection with a bone having a plurality of recesses and disposed in a patient's body, said apparatus comprising an implant having a plurality of spaced apart recesses extending into said implant from a side surface of said implant, and connector means for interconnecting said implant and the bone in the patient's body, said connector means includes a plurality of spaced apart bodies of cement, each of said bodies of cement having a first end portion with surface means for engaging one of the recesses in the bone in the patient's body and a second end portion disposed in one of said recesses of said plurality of recesses in said implant, said implant includes a plurality of ridges each of which projects from said side surface of said implant and extends around an opening to one of said recesses in said implant, each of said ridges having surface means for engaging a recess in the bone in the patient's body.

* * * * *